United States Patent [19]
Bremmer et al.

[11] Patent Number: 5,872,261
[45] Date of Patent: Feb. 16, 1999

[54] PREPARATION OF SULFO-N- HYDROXY SUCCINIMIDE SALTS WITH INTERMEDIATE FORMATION OF DIESTER

[75] Inventors: Martin Lee Bremmer, Rockford; Marty Carey Wilkes, Rockton, both of Ill.

[73] Assignee: Pierce Chemical Company, Rockford, Ill.

[21] Appl. No.: 933,266

[22] Filed: Sep. 18, 1997

[51] Int. Cl.$^6$ .................................................. C07D 207/46
[52] U.S. Cl. ...................... 548/542; 548/544; 548/545; 548/547
[58] Field of Search .................... 548/542, 544, 548/545, 547

[56] References Cited

U.S. PATENT DOCUMENTS

| | | | |
|---|---|---|---|
| 4,540,778 | 9/1985 | Tessler et al. | 536/114 |
| 5,493,031 | 2/1996 | Govindan | 548/542 |
| 5,536,643 | 7/1996 | Mock | 435/7.25 |

FOREIGN PATENT DOCUMENTS

| | | | |
|---|---|---|---|
| 1/206253 | 3/1991 | Japan | C07D 207/416 |

OTHER PUBLICATIONS

"EZ–Link Biotinylation Reagents Reactive Toward Amines", *Biotinylating Reagents*, Pierce 1997 Product Catalog, 22 pages, (1997).

Akiyama, M., "Synthesis of N–Hydroxymaleimide and N–Hydroxyitaconimide and their Related Derivatives", *J.C.S. Perkin I.*, pp. 2122–2125, (Oct. 22, 1979).

Akiyama, M., et al., "A New Approach to the Polymer Reagent for Peptide Synthesis: Preparation of N–Hydroxysuccinimide Ester Polymers Via Polymerizable Active Esters", *Tetrahedron Letters*, No. 13, pp. 1015–1018, (1976).

Hess, R., et al., "Covalent Immunochemical membrane Labeling of Viable Cells with K698–T708, a Simian Virus 40 Tumor Antigen–Derived Peptide", *Peptide Research*, vol. 7, No. 3, pp. 146–152, (1994).

Kung, C.E., et al., "Interactions Between Sufactand Alkyl Sulfo–N–Succinimidyl Esters and Collagen Fibrils", *JALCA*, vol. 88, pp. 12–24, (1993).

Micich, T.J., et al., "Soap–Based Detergent Formulations. XVI. Surface Active Sulfosuccinimides", *Journal of The American Oil Chemists' Society*, vol. 52, pp. 451–454, (Nov. 1975).

Mikolajczyk, M., et al., "Recent Developments in the Carbodiimide Chemistry", *Tetrahedron Report R101*, vol. 37, pp. 233–284, (1981).

Narita, M., et al., "The Dehydration of N–Benzyloxy and N–Hydroxymaleamic Acid and the Isomerization of N–Benzyloxyisomaleimide", *Bulletin of the Chemical Society of Japan*, vol. 44, pp. 437–441, (1971).

Staros, J.V., "Membrane–Imperameant Cross–Linking Reagents: Probes of the Structure and Dynamics of Membrane Proteins", *Accounts of Chemical Research*, vol. 21 No. 12, pp. 435–441, (Dec. 1988).

Staros, J.V., "N–Hydroxysulfosuccinimide Active Esters: Bis(N–Hydroxysulfosuccinimide) Esters of Two Dicarboxylic Acids Are Hydrophilic, Membrane–Impermeant, Protein Cross–Linkers", *Biochemistry*, vol. 21, pp. 3950–3955, (1982).

Wang, S.S., et al., "Enhancement of Peptide Coupling Reactions by 4–dimethylaminopyridine", *Int. J. Peptide Protein Res.*, vol. 18, pp. 459–467, (1981).

*Primary Examiner*—Johann Richter
*Assistant Examiner*—Jane C. Oswecki
*Attorney, Agent, or Firm*—Schwegman, Lundberg, Woessner & Kluth, P.A.

[57] ABSTRACT

A process is described for rapid preparation of pure sulfo-N-hydroxysuccinimides. The process may comprise the steps of:

a) esterifying a sulfo-succinic acid to form a diester first product, and b) reacting said diester first product with hydroxylamine to form a sulfo-N-hydroxy succinimide.

22 Claims, No Drawings

PREPARATION OF SULFO-N- HYDROXY SUCCINIMIDE SALTS WITH INTERMEDIATE FORMATION OF DIESTER

BACKGROUND OF THE INVENTION

1. Field of the Invention

The present invention relates to a method for the synthesis of sulfo-N-hydroxy succinimide salts, novel reduced-impurity or impurity-free salts, and intermediate succinic diester sulfonate salts.

2. Background of the Art

Sulfo-N-hydroxy succinimides (often referred to as "Sulfo-NHS" or "S-NHS"), including the acid and salt counterparts, have a wide range of utility in a number of broad commercial areas, including but not limited to reagents for the manufacture of biotinylation reagents, oil well drilling agents, chemical and biological assay reagents, crosslinking agents for organic biological systems or polymer systems, side chain modifying agents, solubilizing agents, reactants, markers, and the like. The class may be generally represented by the formula below, representing the central nucleus of sulfo-N-hydroxysuccinimides:

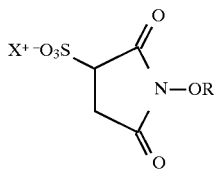

Wherein $X^+$ is a cation and R is H or an organic group.

The compounds may also be described by the formula below, representing the central nucleus:

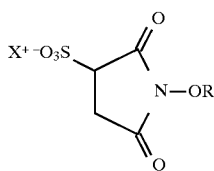

Wherein $X^+$ is a cation and R is H or an organic group, or especially any organic group formed from a compound R—OH wherein R—OH is an acid, and the OH (hydroxyl) which, when symbolically extracted leaves the group R— to form an ester in the compound. Examples of preferred R—OH compounds are acetic acid, LC-biotin suberic acid, biotin, suberic acid, 4-[N-maleimidomethyl]-cyclohexane-1-carboxylic acid, and the like. The 2- and 3- positions on the central nucleus may also be substituted. The cation may be $H^+$, monovalent cations (such as $H^+$, $Na^+$, $Li^+$, $K^+$, $NH_4^+$, $C_s^+$, other inorganic cations, organic cations, etc.), or polyvalent cations (including divalent cations) in which the remaining charge is satisfied by other anions (e.g., halides, nitrates, sulfates, phosphates, etc.) or forms a bis- or tris-configuration with other Sulfo-NHS anions. This class of compounds is relatively expensive, mainly because of the expensive synthetic procedures which must be taken to obtain the product. Existing synthetic procedures must not only use a large number of reagents and involve a large number of synthetic steps, but the procedures involve the use of large volumes of solvents and different solvents which must be stripped after various steps as well as at the end of the procedure. The process cost involved in recapturing and stripping of the solvents is quite significant, and with increasing environmental concerns, the requirements for avoiding release of solvents into the atmosphere have become more strict and therefore more costly.

A typical synthetic process for the synthesis of sulfo-N-hydroxysuccinimide salt is known to follow the following route:

Maleic anhydride:

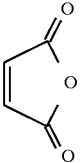

is reacted with furan:

to form a Diels-Alder reaction product:

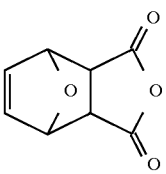

This intermediate product is extremely hazardous and special precautions are required in its handling. Workers must be protectively clothed and may even be required to wear full closure protective gear (e.g., full body suits), including self-contained helmets and at least filters, if not self-contained air supplies. The crystals formed are hazardous to the eyes and are easily propelled and carried by air currents. Even removal of protective garments can be hazardous because of clinging crystalline product which can be put into the air by movement of the clothing. The Diels-Alder product is then reacted with hydroxylamine (e.g., from the hydrochloride salt).

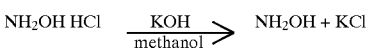

This step is done with potassium hydroxide and methanol (precipitating potassium as potassium chloride) producing an N-Hydroxy succinimide adduct:

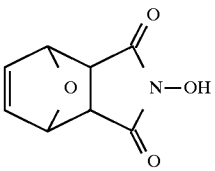

This product is usually washed in toluene and hexane. The N-hydroxy succinimide adduct is then reacted at the hydroxyl group. This reaction is performed by combining the adduct with phenylchloroformate

(which is a strong lachrymator) in various combinations of triethylamine, dichloromethane, toluene and hexane and sometimes dimethyl formamide to produce the next intermediate product:

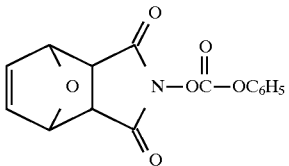

This intermediate product is in turn dissolved in a hydrocarbon solvent, e.g., a non-polar hydrocarbon solvent (e.g., decane) and heated to elevated temperature to form the next intermediate by removal of the protecting group.

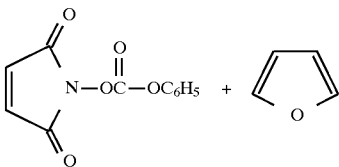

The temperature is elevated to about 170° C., which is above the flashpoint for decane (46° C.). The literature also shows the use of nitrobenzene as the solvent in this step. The reaction product tends to be a black, tarry product as result of using this commercially difficult step. t-Butyl catechol may be used as an antioxidant in this step.

This last intermediate is then reacted with sodium metabisulfite in ethanol to form the sodium salt of sulfo-N-hydroxysuccinimide, which is precipitated as an amorphous solid from aqueous methanol, isopropanol, and washed with acetone:

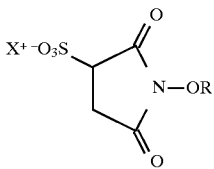

wherein $X^+$ is any cation.

This product is produced in about 95–98% purity as an amorphous solid. Even after repeated purification, there is a clear presence of the succinimide counterpart:

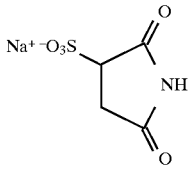

in the final product. Overall yield of the process from the original maleic anhydride is about 25–28% theoretical, and the complete time of the process is about 50 days. Numerous solvent strips must occur, and a kilogram of product is usually produced in reaction vessels of fifty liters or more.

It therefore can be seen that the entire synthetic route is complex, has toxicity, environmental and hazard concerns throughout, is expensive, and is time consuming. Improved methods of synthesis are clearly desirable.

The methyl diester of sulfosuccinate has been reported in the literature, mainly as a copolymer or coating composition, as shown in FR 2 292 314 (copolymer); JP 87-83257 (corrosion inhibitor); JP 88-307097 (alkali metal alkylsuccinates in coatings and adhesives); and JP 89-84305 (anticlouding compositions of the sodium salt of dimethylsuccinate).

In copending U.S. Pat. application Ser. No. 08/932,851, titled "PREPARATION OF SULFO-N-HYDROXY SUCCINIMIDE SALTS," filed the same day as this application in the names of Marty Wilkes and Martin Bremmer bearing Attorneys Docket Number SLWK 544.005US1, the salt of a sulfonated succinic acid is cyclized (e.g., with a Blanc reaction), then converted to novel sulfonated hydroxamic acids by reaction with hydroxylamine, and the novel hydroxamic acid is then cyclized (e.g., by dehydration) to the sulfo-N-hydroxysuccinimide salt. This is a substantially improved method of synthesis over the prior art, but any other advance over the prior art is also useful.

BRIEF DESCRIPTION OF THE INVENTION

The present invention describes a novel method for the synthesis of sulfo-N-hydroxy succinimide salts in which commercially available sulfosuccinic acid salt in an aqueous medium is heated in the presence of an alcohol to form a diester of the succinic acid sulfonate. The diester is then reacted with hydroxylamine (e.g., from the hydrochloride salt) (e.g., in an alkaline buffered aqueous environment, e.g., at room temperature) to form the sulfo-N-hydroxy succinimide. This is an extremely simple and direct process that does not produce a significant level of irremovable impurities.

DETAILED DESCRIPTION OF THE INVENTION

The synthetic procedure of the present invention comprises fewer steps, can be performed in a batch process, requires fewer solvents, and produces novel intermediates and products without similar impurities as compared to processes of previous commercial use. Fewer hazardous materials are synthesized and used, and the process may be performed in a few days (e.g., 2–3 days) as compared to the approximate 50 days used for alternative procedures. Additionally, kilogram product amounts can be produced in a continuous five liter batch process.

One process of the present invention may be described as a synthetic process comprising the steps of:
  a) diesterifying a sulfo-succinic acid compound to form a diester first product (e.g., a diester sulfosuccinate), and
  b) reacting the diester with hydroxylamine hydrochloride (added or formed in situ, as by the combination of $NaNO_2$ and $Na_2SO_3$), forming the sulfo-N-hydroxysuccinimide.

Another process of the present invention may be described as a synthetic process comprising the steps of:
  a) reacting a sulfosuccinate diester with hydroxylamine (e.g., hydroxylamine hydrochloride, added or formed in situ, as by the combination of $NaNO_2$ and $Na_2SO_3$), to form the corresponding sulfo-N-hydroxysuccinimide.

It is not certain what the reaction mechanism is in the conversion of the diester to the sulfo-N-hydroxy succinimide, but it is surmised that a sulfo-hydroxamic acid ester is formed and that this sulfohydroxamic acid is dehydrated/cyclized (e.g., by ester hydrolysis) to form the sulfo-N-hydroxysuccinimide.

This part of the reaction scheme in the process is theoretical as to its mechanism, but the process may continue from the diester to the Sulfo-N-hydroxysuccinimide wherein a sulfo-hydroxamic acid is cyclized, as by ester hydrolysis and/or dehydration, to form a monocyclic sulfo-N-hydroxysuccinimide, wherein the sulfo-N-hydroxy succinimide comprises the general nucleus of:

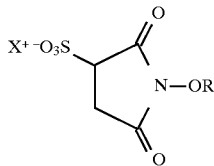

wherein R is as defined as above.

The cyclization, e.g., by dehydration, of the sulfo-hydroxamic acid may occur in the presence of methanol, water, acetic acid, acetic anydride, dicyclohexylcarbodiimide and/or carbonyldiimidazole, as well as any other medium which assists or acts in the dehydration of the hydroxamic acid. The dehydration may be effected merely by leaving the hydroxamic acid in a solution of the additional material, as at room temperature in water, or at slightly elevated temperatures in water. This process is in contrast to the copending U.S. Patent Application of Marty Wilkes and Martin Bremmer. The formation of the sulfohydroxysuccinimide is there effected by the ring-opening cyclic derivative of the sulfo-succinic acid in the presence of hydroxylamine acid complex to form a sulfo-hydroxamic acid. That reaction is performed in the presence of excess alcohol to produce a sulfo-hydroxamic acid ester (e.g., usually a half ester) as a partial product. This ester subsequently performs in essentially the same manner as the acid in conversion to the sulfosuccinimide in the copending process.

The diesters formed during the process of the present invention may be generally described as compounds having the core structure or general nucleus of:

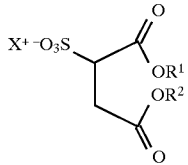

wherein $X^+$ is any cation (as described above), $R^1$ and $R^2$ are independently selected from the group consisting of aliphatic and aromatic groups, especially alkyl and aryl groups, and most particularly alkyl groups of 1 to 8 carbon atoms and phenyl groups.

In the practice of the present invention, the alcohol used to form the diester is preferably methanol, but any alcohol (e.g., C1 to C30, preferably C1 to C8, more preferably C1 to C4) or even glycols (e.g., of 2 to thirty carbon atoms) may be used in this step, since the esterifying moiety is subsequently removed during cyclization or dehydration (e.g., of the hydroxamic acid, if formed). Because of the relatively low number of steps and the reduced amount of residues, waste material and numbers of solvents, the alcohol or glycol is reformed during the dehydration, and this may be readily recovered. This further reduces costs by recycling the alcohol or glycol and avoiding its release into the environment.

The sulfo-N-hydroxysuccinimide, as elsewhere indicated herein, is present in the absence of the hydrogen (the corresponding sulfosuccinimide [NH] compounds) analogs. By further separation and control of enantiomeric components, the sulfo-N-hydroxysuccinimide may have proportions of R and S enantiomers of the sulfo-N-hydroxysuccinimide present, for example, as 100 to 55% or 100 to 50% R or S enantiomers, and may be present as a white, crystalline powder. The sulfo-N-hydroxysuccinimide in any of these forms may be present in the absence of sulfo-N-succinimide (e.g., hydrogen) analogs.

The process may begin with the appropriate sulfosuccinic acid, purchased commercially or formed by the sulfonation of succinic anhydride with sulfur trioxide. The first reagent is a compound having the basic core structure:

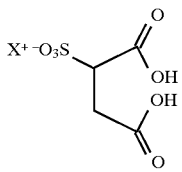

where $X^+$ is any cation, preferably a monovalent cation such as $H^+$, $Na^+$, $Li^+$, $K^+$, $NH_4^+$, etc.

Substitution of compounds is usually expected within the art. To reflect this fact, the term having a core structure or central nucleus (e.g., for Formula I) therefore includes such general substitution as is understood to be acceptable within the art, such as:

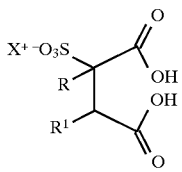

FORMULA I wherein R is H or any other desired substituent. For example, R may be alkyl, alkoxy, halo (I, Cl, Br, F), cyano, alkenyl, aryl (such as phenyl), etc. Likewise, $R^1$ may be hydrogen, alkyl, alkoxy, halo (I, Cl, Br, F), cyano, alkenyl, aryl (e.g., phenyl), etc. Where the terminology 'a compound of the formula' is used, that terminology excludes any substitution not specifically included in the description, e.g., allowing only the inherently understood $R^1$ at the position between the attachment of the sulfonate and the carboxy group. Likewise, the terminology of a 'core formula' or 'central nucleus' could prevent any substitution where a double bond was inserted into the backbone of the hydrocarbon chain of the compound.

Where the term 'core structure' or 'groups' is used, the formula includes any substitution which does not change the actual atoms and bond structure shown. That is, for example with the succinimide and hydroxamic acid, on the unsubstituted portion intermediate the point of attachment of the sulfonate group and the carbonyl, any substitution may be present. Where the terminology a 'compound of the formula' is used, that terminology excludes any substitution not specifically included in the description, e.g., allowing only the inherently understood H at the position between the attachment of the sulfonate and the carboxy group. Likewise, the terminology of a 'core formula' or 'central nucleus' could prevent any substitution where a double bond was inserted into the backbone of the hydrocarbon chain of the compound.

These hydroxamic acids are novel compounds which have not been reported in the literature and first encountered in the above-identified copending U.S. Patent Application in the name of Marty Wilkes and Martin Bremmer. The hydroxamic acids may be generally described as compounds comprising the central nucleus of:

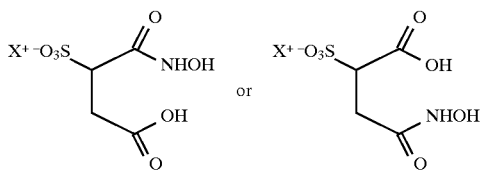

These compounds exist in many tautomeric and enantiomeric forms (For example, the R plus S "chiral center" existing at the point of attachment of the sulfonate group). The tautomeric forms include, for example:

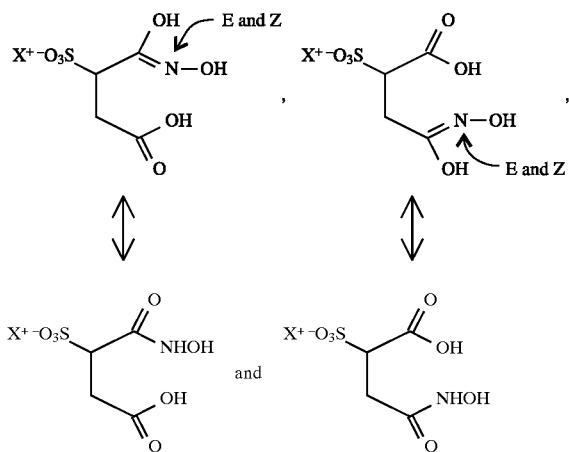

Enolization may also occur in central nuclei such as:

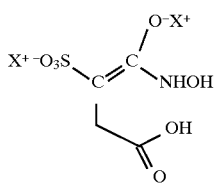

wherein each $X^+$ is independently a cation.

All of these structural variants of the sulfo-NHS compounds are of course expected to be potentially or statistically present as part of any composition containing the primary sulfo-NHS compound of interest, the presence of these variants being at least partially dependent upon the environment, conditions, pH or other system influences on the composition.

At least three other distinguishing aspects of the present invention are noteworthy. These aspects may be individually or jointly present in the compositions of the invention. As previously noted, the process of the prior art used to produce sulfo-NHS produced the succinimide analog (sometimes referred to herein as the hydrogen analog of the hydroxysuccinimide) of the sulfo-NHS compound as a by-product, that succinimide compound being represented by the formula:

wherein the sodium cation may be $X^+$ or any cation as previously defined. This hydrogen analog of the succinimide is present in amount greater than 1.0% by weight (even up to 5% by weight) of the sulfo-NHS compound, even after repeated purification in the attempt to produce a pure sulfo-NHS composition according to the process of the prior art. Commercial sulfo-NHS contains this impurity, and of the 2–5% impurity in the commercial sulfo-NHS composition, this imide compound may be the largest contaminant. The process of the present invention produces a route to the sulfo-NHS compound and class of compounds which does not produce the imide contaminant. Therefore sulfo-NHS compositions which do not contain the imide counterpart are novel and, to date, have been produced only by means of the process de scribed in the present invention. The sulfo-NHS compounds of the present invention therefore may be characterized as novel by the presence of less than 1% by weight of the succinimide (hydrogen) counterpart, preferably less than 0.5% or less than 0.25%, and most preferably less than 0.1 down to 0% by weight of the sulfo-succinimide relative to the weight of the sulfo-N-hydroxysuccinimide.

Secondly, the resulting product of the process of the prior art which produces sulfo-NHS and the commercially available sulfo-NHS materials are amorphous solids. This is thought to be a result of the particular precipitation step used in the final step of the prior art process. The continuous batch process of the present invention produces sharp, white crystals. The clearly crystalline form of the sulfo-NHS compounds produced by this process is also distinct from the amorphous solid sulfo-NHS compounds produced by the prior art process.

Additionally, the sulfo-NHS compounds of the present invention may be separated into the separate enantiomers by a chiral separator. The R and S enantiomers may be separated into more highly purified isomers. This can be very important, as the R and S enantiomers will normally be used to make conjugates for use in assays, e.g., blotting or Elisa-based immunoassays, etc. An unpurified mixture of enantiomers may provide a material with only 50% activity, especially if only one of the R and S enantiomers is reactive towards a particular modification site. By providing a sulfo-NHS composition which may selectively contain higher proportions of R or S enantiomers, up to nearly 100% of either of the enantiomers, the resultant conjugates may be created to form enhanced functional systems. This can enable systems which are tailored for their degree of activity, without having to alter the remaining portions of the composition. For example, if an assay system were provided with a nominal activity of 10, using a 50/50 mixture of R and S enantiomers, the activity might be adjusted from 0 to 20 by appropriate selection of concentrations of the R or S enantiomer which was active in a particular assay. As previously mentioned, this chiral separation may be performed in a conventional manner.

EXAMPLES

Example 1

Preparation of SNHS

Sulfosuccinic anhydride sodium salt (2.56 g) and hydroxylamine hydrochloride (2.13 g) are heated in DMAC (30 ml) to 80 C. TLC after 30 min shows formation of the known UV active sulfo-NHS. TLC system: 35–40% methanol in acetone or 5% water in methanol or 6% water in acetone; silica gel plates. The product was not isolated from this reaction.

Example 2

Preparation of SNHS

The hydroxamic acid (237 g) in glacial acetic acid (700 g) is heated to 80 C. for 2 hours under nitrogen. The reaction mixture is cooled to room temperature and filtered to give 68 g of SNHS as a white solid. The filtrate is diluted with 1 liter of acetone and product is purified by crystallization from 20% water in acetic acid.

Example 3

Preparation of SNHS via Diester

Sulfosuccinic acid (70% in water, 211 g, 0.75 mol) and methanol (256 g, 10.7 eq) are combined in a 1 liter flask; the reaction exotherms as the formation of methyl ester starts. The solution is stirred overnight at room temperature. Hydroxylamine hydrochloride (54.7 g, 0.79 mol, 1.05 eq) is added followed by sodium hydroxide pellets (34 g). The reaction exotherms to 40 C. upon addition of the base. TLC analysis (6% water in acetone, silica gel plate) after stirring 3 days indicates formation of the UV active sulfo-NHS. TLC after 4 weeks clearly shows the UV active sulfo-NHS along with permanganate active hydroxamic acid/ester. TLC Rf values after two elutions: S-NHS=0.6–0.7 streak, UV active; hydroxamic acid/ester: Rf=0.2, non-UV active, potassium permanganate active.

Example 4

Preparation of SNHS via Diester

Sulfosuccinic acid (70% in water, 56 g, 0.2 mol) and methanol (100 ml, 12.3 eq) are combined in a 250 ml flask; the reaction exotherms as the formation of methyl ester starts. The solution is refluxed for two hours and then evaporated on a rotary evaporator to remove water and methanol. The product ester is a clear colorless liquid of moderate viscosity.

The product is treated with 160 g of a 5.5 wt. % solution of hydroxlamine in methanol. The reaction exotherms immediately as the hydroxylamine is added. TLC analysis (6% water in acetone, silica gel plate) after stirring overnight indicates formation of the UV active sulfo-NHS. TLC after 3 days clearly shows the UV active sulfo-NHS. TLC Rf values: SNHS=0.6–0.7 streak, UV active.

What we claim is:

1. A synthetic process comprising the steps of:
   a) esterifying a sulfosuccinic acid to form a diester first product, and
   b) reacting said diester first product with hydroxylamine to form a sulfo-N-hydroxy succinimide.

2. A synthetic process of claim 1 wherein esterifying a sulfosuccinic acid to form a diester first product comprises:
   a) esterifying a sulfosuccinic acid having the central nucleus of:

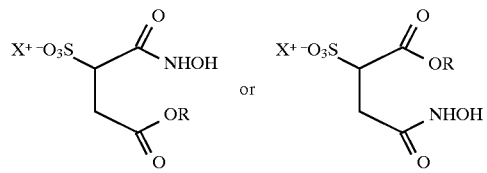

to form a diester first product, wherein $X^+$ is a cation.

3. The process of claim 1 wherein said hydroxylamine is added to said diester first product.

4. The process of claim 1 wherein said hydroxylamine is formed in the presence of said diester first product.

5. The process of claim 1 wherein a sulfo-hydroxamic acid is formed in a reaction of said diester first product with hydroxylamine to form a sulfo-N-hydroxy succinimide.

6. The process of claim 5 wherein said sulfo-hydroxamic acid comprises a compound of the general formula:

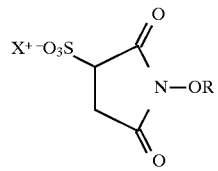

wherein $X^+$ is a cation, and R is hydrogen or alkyl group.

7. The process of claim 5 wherein said sulfo-hydroxamic acid is cyclized to form a monocyclic sulfo-N-hydroxysuccinimide.

8. The process of claim 1 wherein said sulfo-N-hydroxy succinimide comprises an ester compound having the general formula of:

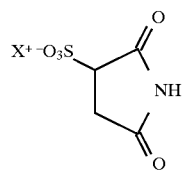

wherein R– is an organic group which completes the ester compound and $X^+$ is a cation.

9. The process of claim 7 wherein said cyclization of the sulfo-hydroxamic acid occurs in the presence of methanol, water, acetic acid, dicyclohexylcarbodiimide and/or carbonyldiimidazole.

10. The process of claim 1 wherein said sulfo-N-hydroxysuccinimide is produced in the absence of a sulfo-succinimide of the formula:

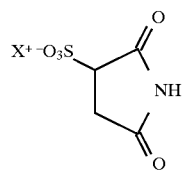

wherein $X^+$ is a cation.

11. The process of claim 1 wherein said diester first product comprises a compound having the formula:

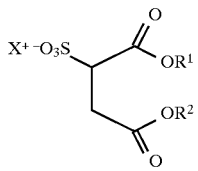

wherein $X^+$ is a cation, and $R^1$ and $R^2$ are independently selected from the group consisting of alkyl and aryl groups.

12. The process of claim 2 wherein said diester first product comprises a compound having the formula:

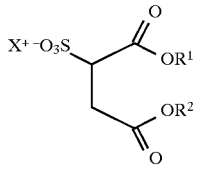

wherein $X^+$ is a cation, and $R^1$ and $R^2$ are independently selected from the group consisting of alkyl and phenyl groups.

13. A The process of claim 5 wherein said diester first product comprises a compound having the formula:

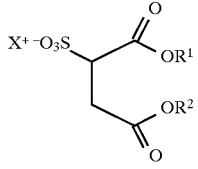

wherein $X^+$ is a cation, and $R^1$ and $R^2$ are independently selected from the group consisting of alkyl and aryl groups.

14. The method of claim 1 wherein the sulfo-N-hydroxysuccinimide has proportions of R and S enantiomers of the sulfo-N-hydroxysuccinimide which are present as 100 to 50% R or S enantiomers.

15. The method of claim 1 wherein the sulfo-N-hydroxysuccinimide is present in the absence of sulfo-succinimide.

16. The method of claim 15 wherein the sulfo-N-hydroxysuccinimide has proportions of R and S enantiomers of the sulfo-N-hydroxysuccinimide which are present as 100 to 50% R or S enantiomers.

17. A process for synthesizing sulfo-N-hydroxysuccinimides, said process comprising the step of:

a) reacting a sulfosuccinate diester with hydroxylamine to form a sulfo-N-hydroxysuccinimide.

18. The process of claim 1 wherein said hydroxylamine comprises hydroxylamine hydrochloride, added to said sulfosuccinate diester or formed from $NH_2OH \cdot HCl$ and a base.

19. A synthetic process comprising the steps of:

a) esterifying a sulfo-succinic acid compound to form a diester first product, and b) cyclizing said diester first product to form a sulfo-N-hydroxy succinimide.

20. A synthetic process comprising the step of cyclizing a diester of sulfosuccinic acid to form a sulfo-N-hydroxy succinimide.

21. The process of claim 20 wherein said cyclizing is done in the presence of hydroxylamine.

22. The process of claim 21 wherein said hydroxylamine is hydroxylamine hydrochloride.

* * * * *